(12) United States Patent
Shinitzky et al.

(10) Patent No.: US 6,288,047 B1
(45) Date of Patent: Sep. 11, 2001

(54) LIPID-BASED IMMUNE MODULATOR COMPOSITION

(75) Inventors: Meir Shinitzky, Kfar Shmariyahu; Avner Shenfeld, Rehovot, both of (IL)

(73) Assignee: Modus Biological Membranes Ltd., Rehovot (IL)

( * ) Notice: Subject to any disclaimer, the term of this patent is extended or adjusted under 35 U.S.C. 154(b) by 0 days.

(21) Appl. No.: 09/462,582

(22) PCT Filed: May 14, 1998

(86) PCT No.: PCT/IL98/00218

§ 371 Date: Mar. 23, 2000

§ 102(e) Date: Mar. 23, 2000

(87) PCT Pub. No.: WO99/03479

PCT Pub. Date: Jan. 28, 1999

(30) Foreign Application Priority Data

Jul. 16, 1997 (IL) .................................................. 121322

(51) Int. Cl.⁷ .......................... A61K 31/66; A61K 35/78
(52) U.S. Cl. .......................... 514/121; 514/120; 514/810; 514/811; 514/812; 514/885; 424/725; 424/757
(58) Field of Search .................. 424/195.1, 725, 424/757; 514/120, 121, 810, 811, 812, 885

(56) References Cited

U.S. PATENT DOCUMENTS

| | | | |
|---|---|---|---|
| 4,263,286 | * | 4/1981 | Nakajima et al. ...................... 514/78 |
| 5,183,750 | * | 2/1993 | Nishide et al. ........................ 435/134 |
| 5,314,906 | * | 5/1994 | Bonbardelli .......................... 514/411 |
| 5,484,833 | * | 1/1996 | Bombardelli ......................... 424/449 |
| 6,051,564 | * | 4/2000 | Shenfeld et al. ...................... 514/120 |

FOREIGN PATENT DOCUMENTS

| | | | |
|---|---|---|---|
| 2045612 | * | 11/1980 | (GB) . |
| 4211014 | * | 8/1992 | (JP) . |
| WO 95/13808 | | 5/1995 | (WO) . |
| 95/20967 | * | 8/1995 | (WO) . |
| WO 95/20967 | | 8/1995 | (WO) . |
| WO 97/41874 | | 11/1997 | (WO) . |

OTHER PUBLICATIONS

Ohata et al. Life Sciences, vol. 58, No. 1, pp. 29–38, 1996.*
Ohata, Hisayuki, et al., "Lysophosphatidic Acid Sensitizes Mechanical Stress–Induced $Ca^{2+}$Mobilization in Cultured Human Lung Epithelial Cells", *Life Sciences*, v. 58, pp. 29–36 (1996).
Valdivia, L.A. et al., "Perioperative Treatment With Phosphatidic Acid Inhibitor (Lisofylline) Leads to Prolonged Survival of Hearts in Guinea Pig to Rat Xenotransplant Model", *Transplantation Proceeding*, v. 28, pp. 738–739 (1996).
Rice, Glenn, C., et al., "Protection From Endotoxic Shock in Mice by Pharmacologic Inhibition of Phosphatidic Acid", *Medical Sciences*, v. 91, pp. 3857–3861 (1994).
Sakina, M.R. et al., "A Neurophychopharmacological Profile of "CINKARA", A Polyherbal Preparation", *Institute of History of Medicine & Medical Research*, v. 33, pp. 43–46 (1989).
de Stein, Miguelina Levi, et al., "In Vivo And In Vitro Modulation of Central Type Benzodiazepine Receptors By Phosphatidylserine", *Molecular Brain Research*, pp. 9–15 (1989).
Singer, Jack, W. et al., "Inhibitors Of Intracellular Phosphatidic Acid Production: Novel Therapeutics with broad clinical applications", *Oncologic, Endocrine and Metabolic*, pp. 631–643 (1994).

* cited by examiner

*Primary Examiner*—Christopher R. Tate
(74) *Attorney, Agent, or Firm*—Nath & Associates PLLC; Gary M. Nath; Jerald L. Meyer

(57) ABSTRACT

A method of treating an individual with an immune system with decreased activity by administering an effective amount of a lipid preparation derived from a natural source and enriched to contain at least 10% (w/w) phosphatidic acid (PA) is disclosed.

7 Claims, 5 Drawing Sheets

LIPID-BASED IMMUNE MODULATOR COMPOSITION

FIELD AND BACKGROUND OF THE INVENTION

The present invention concerns a composition and method for activation of the immune system. The composition of the present invention is particularly useful for activation of the immune system in a stress situation where the activity of the immune system decreases. A particular example of a stress-induced decrease in activity of the immune system is in the case of smoking cessation.

There are many clinical conditions where the activity of the immune system decreases, thus rendering the individual more susceptible to opportunistic infections. It is also known that stress, such as that resulting from injuries, from rehabilitation, from addiction to a drug, alcohol or smoking, may result in decrease in the immune system's activity, in a matter of minutes. For example, strong infections occurring in the aftermath of a severe injury have been documented.

It is the object of the present invention to provide a composition for enhancing activity of the immune system to render it more active, useful particularly in stressed individuals.

SUMMARY OF THE INVENTION

In accordance with the invention it was surprisingly found that a natural lipid preparation enriched with phosphatidic acid (PA) is capable of activating the immune system. This activity of the PA-enriched lipid preparation which was found to be associated with decrease in activity of the immune system was tested in individuals undergoing a smoking cessation treatment.

In the following, use will be made with several terms, these terms and their meanings in the context of the invention, are as follows:

PA-enriched lipid preparation (PA-E-LP)—a lipid preparation comprising at least 10% (w/w) of PA, preferably within the range of about 20%–75% of PA, out of the total lipid content of the composition. (The concentration indication of "%" given above and below means to denote the number of weight units of an ingredient per 100 weight units of the entire composition (w/w)).

Natural PA-E-LP—a PA-E-EP derived from a natural lipid preparation, e.g. a phospholipid preparation derived from plants, from animal tissue, or any combination thereof. Such a natural phospholipid preparation may typically be derived from soybean, from egg yolk or from animal sera. The natural PA-E-EP is prepared from a natural phospholipid preparation, typically by an enzymatic process. In a natural PA-E-EP, the remainder of the lipids consist primarily of phospholipids although small quantities, e.g. 0.1–10%, of other lipophilic substances, such as cholesterol, fatty acids, etc., may also be included in the preparation.

Stressed individuals—individuals exposed to a situation or a condition such as anxiety, physical injuries, cessation of use of drugs, use of alcohol, smoking, etc. giving rise to stress.

The present invention provides, by one of its aspects a pharmaceutical composition for activating the immune system, comprising a lipid preparation derived from a natural source enriched to comprise at least about 10% PA. preferably at least about 20% PA and most desirably above 50% PA. Typically the concentration of PA, out of the total lipid ingredient, would not exceed 75%.

The composition of the invention is particularly useful in activating the immune system in stress-related conditions involving reduction of the immune system's activity. Examples of such stress conditions are a variety of injuries, cessation of use of drugs, alcohol, smoking, etc.

The present invention further provides a method for activation of the immune system in an individual in need, comprising administering to the individual an effective amount of PA-E-LP, particularly natural PA-E-LP.

The invention still further provides use of said PA-E-LP, and particularly of natural PA-E-LP, for the preparation of a pharmaceutical composition for activation of the immune system.

The term "effective amount" should be understood as an amount of an ingredient sufficient to yield a desired therapeutic effect. For example, administration of an effective amount of the pharmaceutical composition of the invention to an individual results in an increase in the activation level of the immune system. The level of activation may, for example, be measured by the blood plasma level of gamma-interferon ($\gamma$-IFN) which may thus serve as a gauge to determine the effective amount. The term "activation of the immune system" or similar term should be understood as referring to increase in level of activity of immune cells in countering pathogens or pathological processes, increase in level of secretion or production of various cytokines thereby which boost such activities of the immune cells, etc.

The pharmaceutical composition of the invention may typically be orally administered although it may also be formulated for topical or parenteral administration. For oral administration the composition may comprise various flavoring agents, edible colors, etc. Furthermore, the composition for oral use may also6be encapsulated, e.g. in an enterocoated gelatine capsule. The composition may comprise a variety of pharmaceutically acceptable carriers, diluents or excipients, which may be chosen based on the intended mode of administration of the composition.

For parenteral administration the composition will typically be injected intravenously (I.V.). Such a parenteral composition may for example comprise soybean multitriglycerides, egg phospholipids, PA prepared in accordance with the invention, glycerol and distilled water.

A topical composition may be in the form of a gel or a salve and may thus comprise various additives known per se to allow the compositions to obtain such a physical form (e.g. a gelating agent).

The natural PA-E-LP is preferably obtained from a natural phospholipid preparation by enzymatic treatment using a synthetic or natural source comprising the enzyme phospholipase-D. The natural phospholipid preparation may be of vegetable origin, may be of animal origin, or a combination thereof. Typical examples of natural phospholipid preparations useful for the preparation of natural PA-E-LP of the invention are, soya lecithin, egg yolk and phospholipids from animal serum. Examples of phospholipase-D sources, are peanuts, typically ground peanuts or a phospholipase-D fraction derived therefrom. Phospholipase-D or a phospholipase-D source is added in an amount and for a time sufficient to hydrolyze at least about 10% or preferably about 25% and most preferably about 50% of the phospholipids to yield PA-E-LP.

The present invention will now be illustrated in the following nonlimiting examples with occasional reference to the annexed drawings.

EXAMPLE 1

Preparation of PA Mixture (a) Preparation of a Reaction Product

Figure 1:
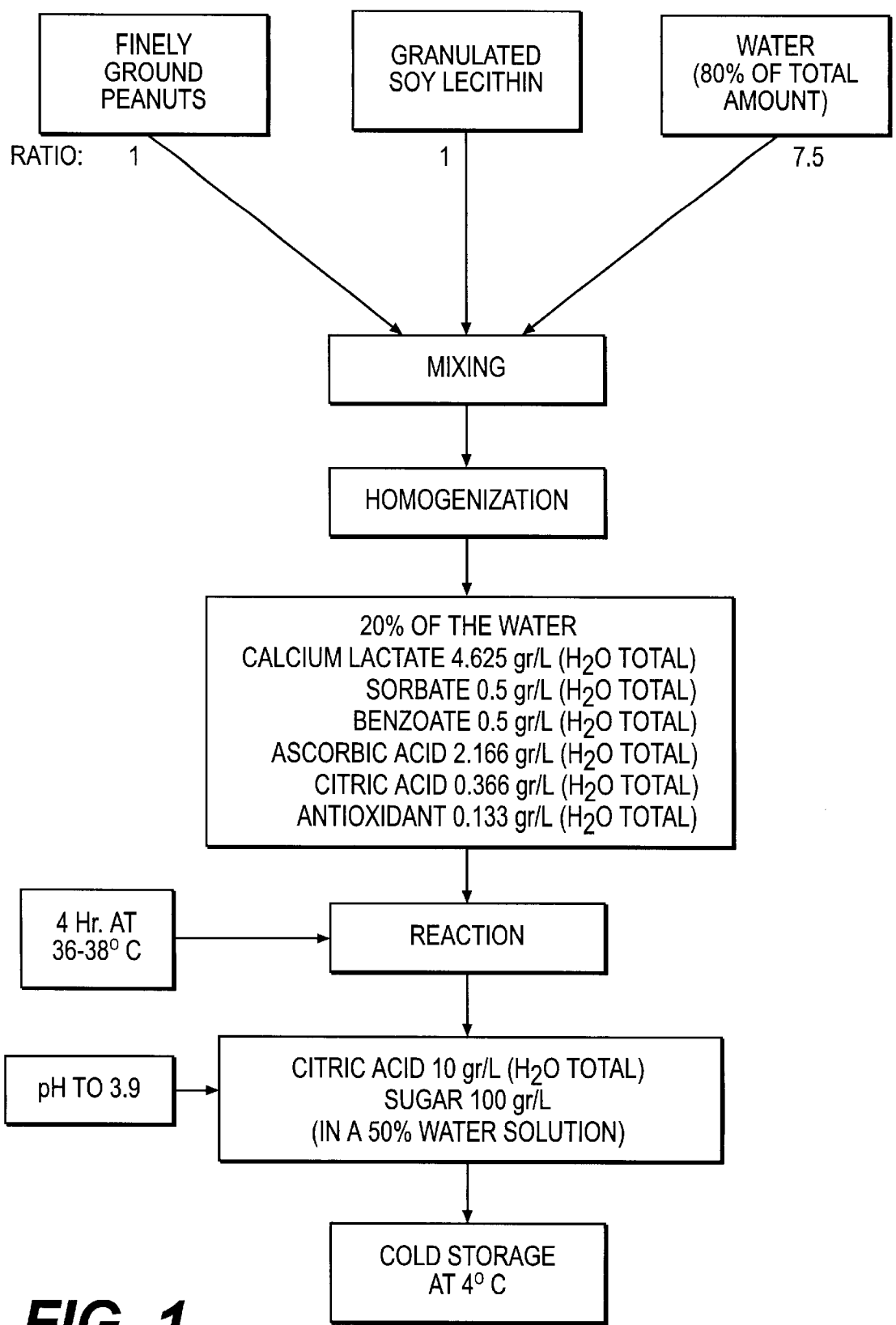
FIG. 1 is a schematic representation depicting the preparation of the PA enriched mixture of the invention. As can be seen in the figure, the ratio of the starting materials (peanuts, soya lecithin and water) is 1:1:7.5, respectively.

FIG. 1 schematically depicts the method of preparation of a PA mixture in accordance with the invention. As can be seen, the starting materials are the following:

1. 150 grams of grained fresh peanuts as an origin of Phospholipase D.
2. 150 grams of granulated soy lecithin as an origin of soybean phospholipids.
3. 1000 ml. to be added to $H_2O$.

The above-mentioned starting materials were mixed in a meat blender, brought to homogenization and then the PH of the mixture was adjusted to a PH of 5.3–5.4 by the addition of calcium lactate, sorbate, benzoate, ascorbic acid, citric acid and an anti-oxidant (each in the amount described in the figure). The mixture was then reacted under continuous mixing for four hours at 36–38° C. after which the pH was once more adjusted to a pH of 3.9 by the addition of citric acid and sugar in amounts described in the figure. The mixture is then stored at 4° C. overnight.

(b) Separation of the Lipid Fraction

Figure 2:
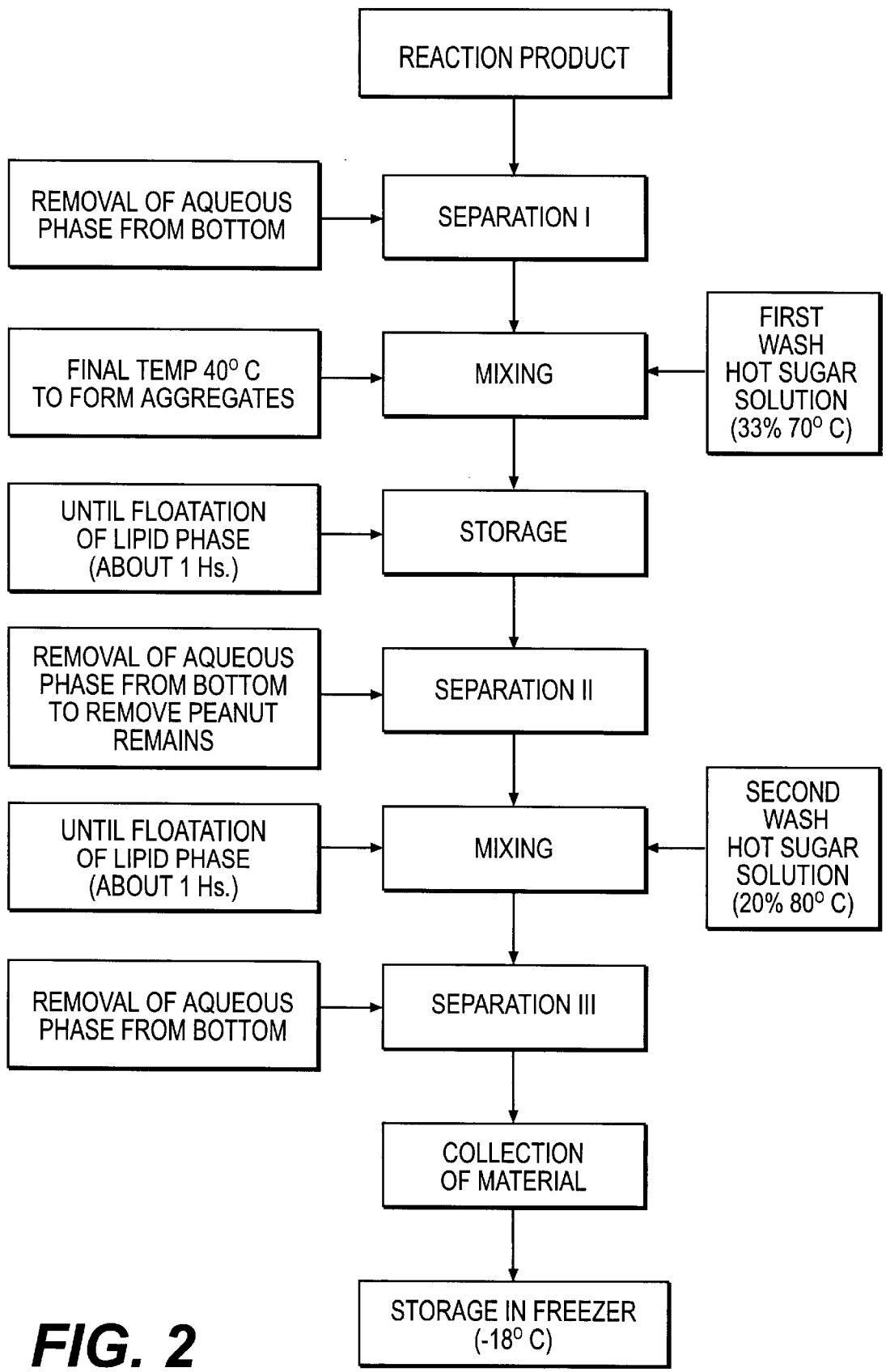
FIG. 2 is a schematic representation depicting the separation of the lipid phase of the PA-mixture prepared by the reaction showed in FIG. 1.

The reaction mixture obtained by the above procedure is then further separated by a procedure depicted schematically in FIG. 2. As seen in the figure, the reaction product is subjected to three main separations (indicated as separations I, II and III in the figure) wherein, generally, in each separation the aqueous phase of the mixture is removed from the bottom until, finally, the separated lipid phase is collected and stored in a freezer (−18° C.).

(c) Preparation of the Lipid Composition for Filling Containers

Figure 3:
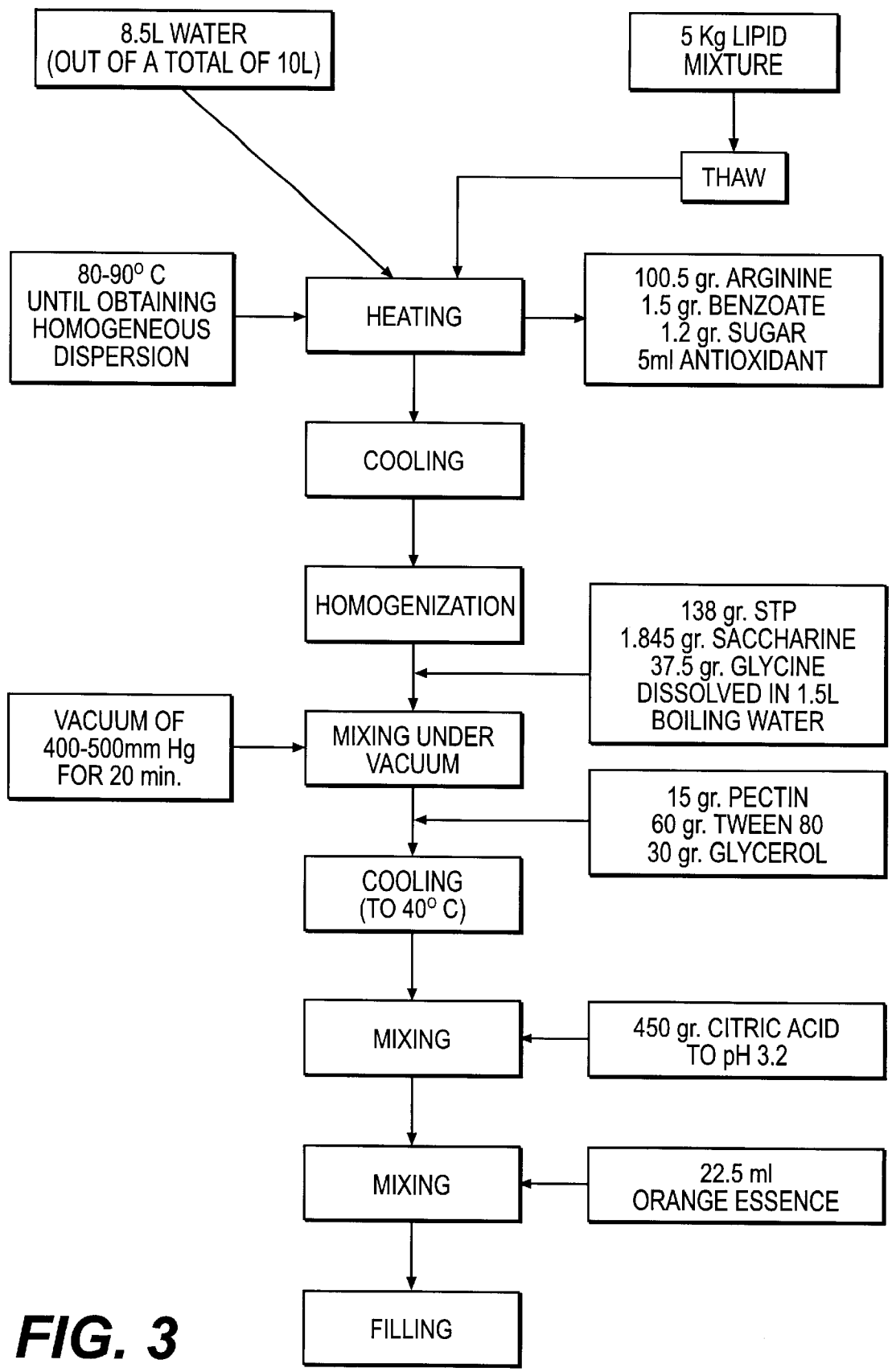
FIG. 3 is a schematic representation depicting the preparation of the PA-mixture of the invention prepared as described in FIGS. 1 and 2 in a suitable form for filling containers.

The lipid mixture obtained by the above separation was subjected to several additional procedures by which it was prepared for filling containers. As seen in FIG. 3, the lipid mixture obtained by the above separation process was first thawed and then treated by heating, cooling, homogenization and mixing as described in FIG. 3 to form a composition suitable for filling containers. Typically the size of the containers are half a liter and the containers are then stored at 4° C.

(d) Preparation of PA Containing Tablets

Figure 4:
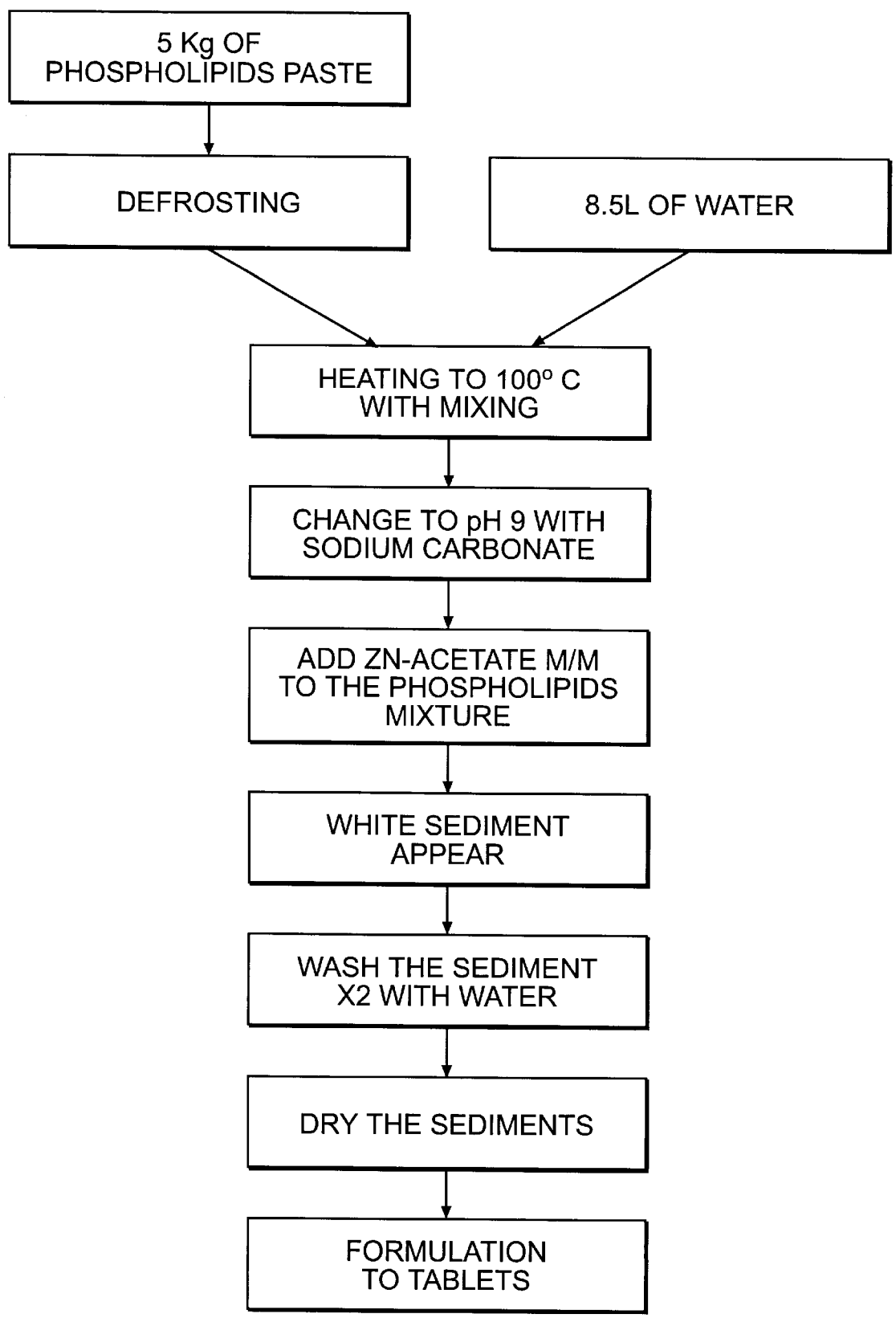
FIG. 4 is a schematic representation depicting the preparation of tablets from the PA-mixture prepared as described in FIGS. 1 and 2.

The PA mixture obtained by the method described in Examples 2(a)–2(c) above and shown in FIGS. 1–3 may also be processed into tablets. The method for preparation of tablets comprising the PA mixture is shown in FIG. 4. As seen in the figure, generally the phospholipid paste obtained by the above process is first defrosted and then heated and the Ph of the mixture adjusted to a high pH of about 9. Following addition of zinc acetate to the mixture a wide sediment appears which after washing and drying is formulated into tablets.

(e) Profile of PA Formation

Figure 5:
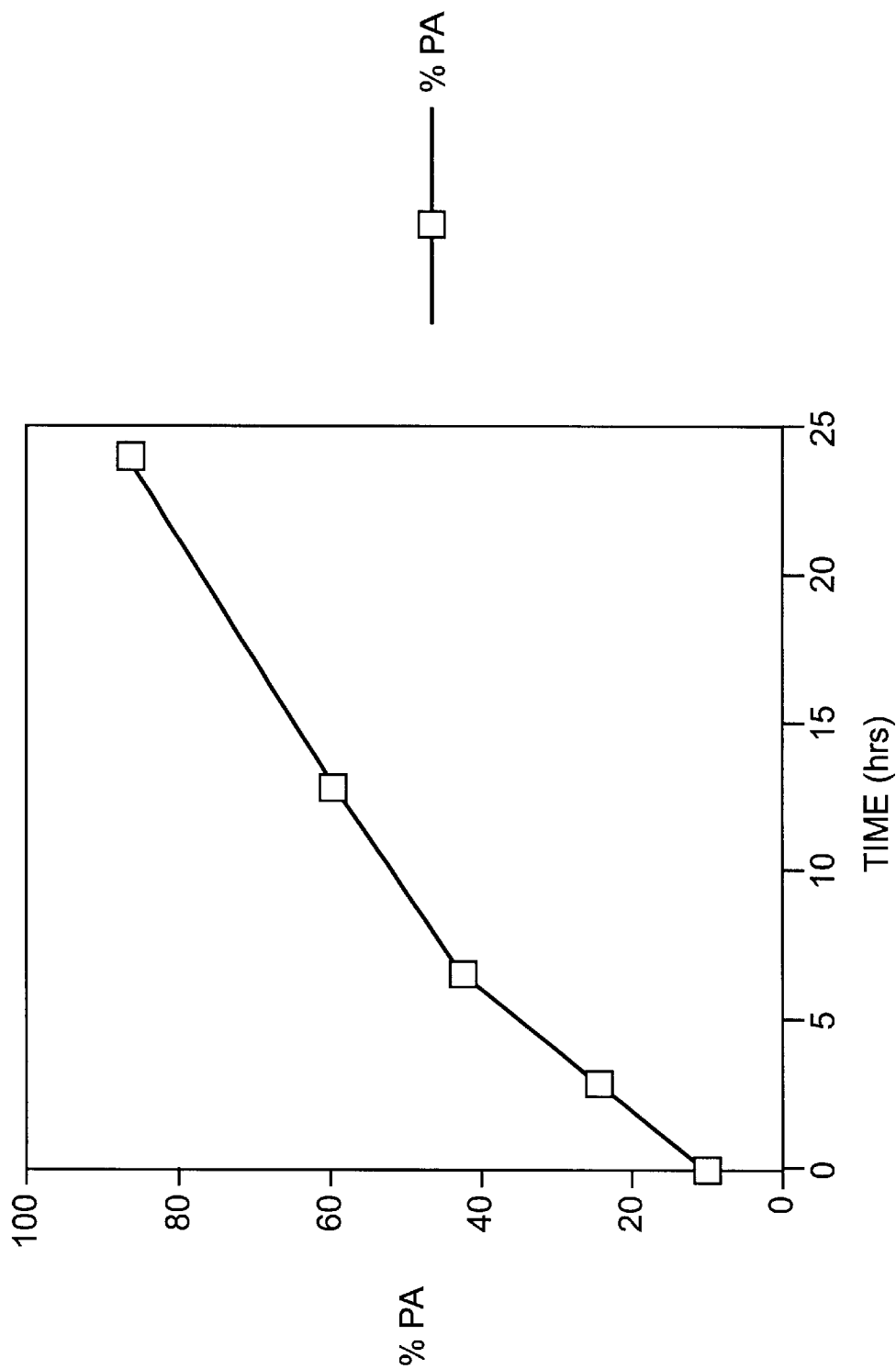
FIG. 5 shows the formation profile of PA during an enzymatic hydrolysis of soybean phospholipids. (The results are present as % from the entire composition).

The profile of formation of PA is depicted in FIG. 5. As can be seen, after about 24 hours, more than 80% of the soybean phospholipid was hydrolyzed yielding a PA enriched preparation.

EXAMPLE 2

Effect of a PA-E-LP Composition in Increasing Gamma-interferon Levels in Individuals Undergoing a Smoking Cessation Treatment (a) Study Design 35 cigarette smokers which of 20 and 40 cigarettes per day, and who volunteered to enroll in the study, were assigned at random into two groups: one group, consisting of 16 individuals, received a daily dose of 12 grams ((taken orally) of PA-E-LP composition prepared in accordance with Example 1, containing 50% PA; and the second group, serving as control, received a placebo treatment. The individuals of both groups ceased smoking during the study.

Concentrations of γ-IFN in plasma were measured in individuals in both groups, before and after the smoking cessation. The γ-IFN level was measured by employing the QUANPIKINE™ (R&D Systems Inc., USA) Kit.

(b) Results

The γ-IFN concentrations in the two groups, before and after the treatment is shown in the following Table 1.

TABLE 1

| -IFN Plasma Concentrations | | | | | | | |
|---|---|---|---|---|---|---|---|
| PA-E-LP Group | | | | Placebo Group | | | |
| Subject Number | Before treatment | After treatment | Difference | Subject Number | Before treatment | After treatment | Difference |
| 3 | 0.6 | 0.5 | −0.1 | 5 | 1.7 | 0.7 | −1 |
| 4 | 0.6 | 0.6 | 0 | 7 | 0.6 | 0.7 | 0.1 |
| 6 | 1.2 | 1.4 | 0.2 | 9 | 0.7 | 0.5 | −0.2 |

TABLE 1-continued

γ-IFN Plasma Concentrations

| | PA-E-LP Group | | | | Placebo Group | | |
|---|---|---|---|---|---|---|---|
| Subject Number | Before treatment | After treatment | Difference | Subject Number | Before treatment | After treatment | Difference |
| 8 | 0.15 | 0.4 | 0.25 | 10 | 3.7 | 0.6 | −3.1 |
| 11 | 1.1 | 1 | −0.1 | 12 | 0.4 | 0.6 | 0.2 |
| 13 | 0.5 | 0.6 | 0.1 | 19 | 1 | 0.3 | −0.7 |
| 14 | 0.8 | 7.3 | 6.5 | 24 | 1.2 | 0.15 | −1.05 |
| 16 | 0.5 | 0.6 | 0.1 | 25 | 0.8 | 1.1 | 0.3 |
| 20 | 0.7 | 0.4 | −0.3 | 26 | 1.8 | 0.7 | −1.1 |
| 30 | 1.5 | 0.9 | −0.6 | 27 | 0.6 | 0.4 | −0.2 |
| 31 | 1 | 2.6 | 1.6 | 29 | 6.1 | 1.1 | −5 |
| 34 | 1 | 0.8 | −0.2 | 32 | 0.5 | 2 | 1.5 |
| 35 | 1.1 | 1.4 | 0.3 | 33 | 0.6 | 0.6 | 0 |
| 38 | 0.7 | 0.8 | 0.1 | 36 | 1.6 | 1.3 | −0.3 |
| 43 | 0.8 | 1.0 | 0.2 | 37 | 0.5 | 0.9 | 0.4 |
| 44 | 1.7 | 1.7 | 1.6 | 39 | 0.8 | 1.2 | 0.4 |
| | | | | 42 | 0.7 | 1.23 | 0.53 |
| | | | | 45 | 0.8 | 0.15 | 0.65 |
| | | | | 46 | 0.15 | 0.15 | 0 |
| Mean | 0.87 | 1.48 | 0.60 | | 1.41 | 0.80 | −0.61 |
| S.D. | 0.39 | 1.75 | 1.68 | | 1.50 | 0.46 | 1.54 |

It can be seen from the above results, the blood plasma γ-IFN concentration rose in the group receiving the PA-E-LP, while the concentration of plasma γ-IFN in the placebo group was lower than its concentration before treatment.

It should be noted, that blood plasma γ-IFN levels are an indication of the activation state of the immune system.

What is claimed is:

1. A method for the therapeutic treatment of an individual with an immune system with decreased activity, comprising administering to the individual an effective amount of a lipid preparation derived from a natural source and enriched to comprise at least 10% (w/w) phosphatidic acid (PA), said treatment resulting in increased activity of the immune system as compared to the immune system activity prior to said treatment.

2. A method according to claim 1, wherein the lipid preparation comprises at least 20% (w/w) PA.

3. A method according to claim 2, wherein the lipid preparation comprises at least 50% (w/w) PA.

4. A method according to claim 1, wherein the individual is a stressed individual and the decreased immune system activity is associated with stress.

5. A method according to claim 4, wherein the stress is the result of smoking cessation.

6. A method according to claim 1, wherein the PA composition is administered orally.

7. A method according to claim 1, wherein the treatment results in enhancing the level of plasma γ-IFN in an individual.

* * * * *